US009790539B2

(12) United States Patent
Russell et al.

(10) Patent No.: US 9,790,539 B2
(45) Date of Patent: Oct. 17, 2017

(54) METHODS AND REAGENTS FOR IMPROVED SELECTION OF BIOLOGICAL MOLECULES

(75) Inventors: Thomas R. Russell, Huntingdon Valley, PA (US); Michael J. Ciocci, Royersford, PA (US); Michael Musick, Mason, OH (US)

(73) Assignee: Russell Biotech, Inc., Doylestown, PA (US)

( * ) Notice: Subject to any disclaimer, the term of this patent is extended or adjusted under 35 U.S.C. 154(b) by 27 days.

(21) Appl. No.: 11/159,957

(22) Filed: Jun. 23, 2005

(65) Prior Publication Data

US 2006/0003371 A1    Jan. 5, 2006

Related U.S. Application Data

(60) Provisional application No. 60/584,409, filed on Jun. 30, 2004.

(51) Int. Cl.
C12Q 1/68 (2006.01)
G01N 33/543 (2006.01)

(52) U.S. Cl.
CPC ....... *C12Q 1/6806* (2013.01); *G01N 33/5434* (2013.01); *G01N 33/54313* (2013.01); *G01N 33/54326* (2013.01)

(58) Field of Classification Search
CPC ............. C12Q 1/6806; G01N 33/5434; G01N 33/54313; G01N 33/54326
USPC ............................... 436/526, 518, 545; 435/6
See application file for complete search history.

(56) References Cited

U.S. PATENT DOCUMENTS

| 4,018,886 | A | * | 4/1977 | Giaever | ........................ 436/526 |
| 4,672,040 | A | * | 6/1987 | Josephson | ..................... 436/526 |
| 5,186,827 | A | | 2/1993 | Liberti et al. | |
| 5,200,270 | A | * | 4/1993 | Ishida et al. | .................. 428/403 |
| 5,238,812 | A | | 8/1993 | Coulter et al. | |
| 5,411,863 | A | | 5/1995 | Miltenyi | |
| 5,466,574 | A | | 11/1995 | Liberti et al. | |
| 5,512,439 | A | | 4/1996 | Hornes | |
| 5,536,644 | A | * | 7/1996 | Ullman | ..................... B03C 1/01 209/214 |
| 5,576,185 | A | | 11/1996 | Coulter et al. | |
| 5,622,831 | A | | 4/1997 | Liberti et al. | |
| 5,744,367 | A | * | 4/1998 | Talley et al. | .................. 436/172 |
| 5,770,388 | A | | 6/1998 | Vorpahl | |
| 6,017,719 | A | | 1/2000 | Tseng-Law et al. | |
| 6,033,574 | A | | 3/2000 | Siddiqi | |
| 6,074,884 | A | | 6/2000 | Siiman et al. | |
| 6,190,870 | B1 | * | 2/2001 | Schmitz et al. | ............. 435/7.23 |
| 6,365,362 | B1 | | 4/2002 | Terstappen et al. | |

(Continued)

FOREIGN PATENT DOCUMENTS

EP    0 877 941 B1    2/2003

OTHER PUBLICATIONS

Zach, M.P. , Penner, R.M. , *Nanocrystalline Nickel Nanoparticles*, Adv Mat; v:878; Dec. 2000.

*Primary Examiner* — Gail R Gabel
(74) *Attorney, Agent, or Firm* — Joseph F. Aceto, Esq.

(57) ABSTRACT

Coated Ferromagnetic Density Particles or Density Particles with binding agents bound thereto capable of binding biological molecules and methods of use and apparatus for means are disclosed. Coated particles coupled to specific binding agents can be used for molecular biology and proteomic applications in research and diagnostics.

20 Claims, 3 Drawing Sheets

(56) References Cited

U.S. PATENT DOCUMENTS

| | | |
|---|---|---|
| 6,672,458 B2 | 1/2004 | Hansen et al. |
| 6,730,230 B2 | 5/2004 | Cook et al. |
| 2002/0058030 A1 | 5/2002 | Monroy et al. |
| 2003/0040129 A1* | 2/2003 | Shah .............................. 436/526 |
| 2004/0023222 A1* | 2/2004 | Russell et al. ..................... 435/6 |
| 2004/0126902 A1* | 7/2004 | Nishiya et al. ............... 436/526 |

* cited by examiner

METHODS AND REAGENTS FOR IMPROVED SELECTION OF BIOLOGICAL MOLECULES

CROSS REFERENCE TO RELATED APPLICATIONS

Priority is claimed to U.S. Provisional Application Ser. No. 60/584,409 filed Jun. 30, 2004, the disclosure of which is incorporated by reference herein in its entirety.

BACKGROUND OF THE INVENTION

Field of the Invention

This invention relates to methods and compositions for selecting biological molecules such as nucleic acids and proteins using coated ferromagnetic density particles (FMP) or density particles (DP) and kits for research, therapeutic and diagnostic uses. More specifically, the invention relates to selection of biological molecules which are not cells, but which include components of cells such as nucleic acids, organelles, proteins, lipoproteins, glycoproteins, peptides, components present in serum or plasma, whether or not of plant, animal, or other living organisms, and similar like substances. Further, the invention relates to large scale chromatographic isolation of proteins including applications in Affinity Chromatography and High Performance Liquid Chromatography.

Description of the Related Art

In the biochemical manipulation of cells and biological molecules (such as but not limited to nucleic acids and/or proteins) it is often desirable to isolate specific cells, specific nucleic acid sequences or specific proteins from complex mixtures for downstream processing using solid phase supports as described herein. Numerous magnetic particle based cell separation technologies based on superparamagnetic particles and ferromagnetic particles exist. Separation of cells by gravity settling using dense particles has also been described. However, in the isolation of biological molecules (nucleic acids and/or proteins) only technologies based on superparamagnetic particles have been described with some success, particularly in DNA applications. To date the use of ferromagnetic particles and dense particles has been confined to the field of cell separation. Some prior literature has suggested that ferromagnetic materials may be used to separate biological molecules, but no specific details have been provided as to how this might be done. More specifically, the mentioned ferromagnetic materials are generally non-specific in nature and could not be used to isolate specific biological molecules.

On the other hand, use of superparamagnetic particles to isolate proteins is well documented. Particles commercially available from Dynal Biotech, as referenced in its 2003 Product catalog have been used for immunoprecipitation and co-immunoprecipitation of pure proteins; to pull down large protein complexes that tend to be broken down by traditional column chromatography techniques; for depletion of proteins; use of GST-fusion proteins applying anti-tag antibodies; immobilization of active enzymes used in production of chemical compounds and foods; to immunoselect proteins for further separation on SDS PAGE and downstream analysis by mass spectrometry; in MALDI-TOF mass analysis; and in various diagnostic applications including immunoassays and bioassays.

Use of superparamagnetic particles to isolate nucleic acids (RNA and DNA) is also well documented. Particles available form Dynal Biotech have been used for the isolation of pure intact mRNA from pure cell populations; mRNA for cDNA libraries; mRNA for RT-PCR and real-time PCR; mRNA for northern blotting; mRNA for microarrays. Such particles have also been used for the isolation of DNA from bacteria and blood and other clinical specimens; for tissue typing; for mutation detection and SNP's analysis. These particles have also been used for isolating RNA and DNA binding proteins using sequences bound to particles that recognize the binding region in the binding protein.

One commonly used solid support for isolating biological materials are superparamagnetic particles that come in various sizes and can be either non-uniform such as those commercially available from Advanced Magnetics, and described in U.S. Pat. No. 4,672,040. Another type of particle are those which are very uniform such as those available from Dynal Biotech and disclosed in U.S. Pat. No. 5,512,439. Other manufacturers of superparamagnetic particles include Miltenyi Biotech, Immunicon Corporation, R and D Systems, Polysciences and Stem Cell Technologies, Inc. The magnetic particles are generally <5 micron in diameter and have a density<1.8 g/cm$^3$.

Another magnetic particle has been described in the literature. These particles are known as ferromagnetic (FMP) particles, are available commercially from TRC Biotech and are described in U.S. Published Application No. 2004-0023222. FMP have been shown to offer advantages over superparamagnetic particles in the field of cell separation. The advantages of FMP for cell separartion applications center around the core particle material, nickel, and three properties of nickel: Density: Nickel has a density of 8.9 g/cm$^3$ which is ~8 times the density of cells and ~6 times the density of current magnetic particles. This difference in density results in very high mixing efficiency which in turn yields very rapid reaction kinetics often on the order of seconds; Magnetics: Because FMP are composed of solid Nickel, the particles are ferromagnetic. The ferromagnetic nature of the particles results in separation times up to ten times faster than current technologies that are based on superparamagnetic particles; and Particle Surface: Non-targeted cells do not stick to FMP because of the characteristics of the metallic particle surface. The particle is uncoated and thus is not composed of organic coatings as is seen with many superparamagnetic particles. As a result only targeted cells are captured.

While U.S. Published Application 2004-0023222 speculates generally about the use of the particles described therein in separating biological molecules, the materials described therein are non-specific to biological molecules and cannot be used to bind specific biological molecules if used in the form described therein. There is no specific disclosure in that application of how such separation of biological molecules might be done with the particles described therein. The comments are merely speculative and later tests have shown that the particles described in the published application cannot be used to separate biological molecules.

In order to more fully appreciate the differences between superparamagnetic particles and ferromagnetic particles, it is important to compare their properties as discussed hereafter.

More specifically, U.S. Pat. Nos. 5,411,863 and 5,466,574 teach that superparamagnetic particles are particles of choice for biological selection applications. Superparamagnetic materials have in recent years become the backbone of magnetic selection technology in a variety of health care and bio-processing applications. Superparamagnetic materials are highly magnetically susceptible, i.e., they become strongly magnetic when placed in a magnetic field but rapidly lose their magnetism when the magnetic field is removed. This property makes it easy to isolate and resuspend biological molecules when the magnetic field is removed.

Superparamagnetism occurs in ferromagnetic materials when the crystal diameter is decreased to less than a critical value. Such materials, regardless of their diameter (about 25 nm to about 100 microns) have the property that they are only magnetic when placed in a magnetic field. The basis for superparamagnetic behavior in ferromagnetic materials is that such materials contain magnetic material in size units below about 20 to about 25 nm, which is estimated to be below the size of a magnetic domain. A magnetic domain is the smallest volume for a permanent magnetic dipole to exist. Ferromagnetic materials, as contrasted to superparamagnetic materials, are strongly susceptible to magnetic fields and are capable of retaining magnetic properties when the field is removed. Ferromagnetism occurs only when unpaired electrons in the material are contained in a crystalline lattice thus permitting coupling of the unpaired electrons. The prior art teaches that ferromagnetic particles with permanent magnetization have considerable disadvantages, for example, as discussed in U.S. Pat. No. 5,411,863. and U.S. Pat. No. 5,466,574 for applications in biological molecule selection, since suspensions of these particles easily aggregate following exposure to a magnetic field due to their high magnetic attraction for each other. For this reason ferromagnetic particles have not been used for biological (nucleic acid selection/protein selection) applications.

In a further development as discussed in Published Application No. 2004-0023222, FMP have been shown to retain the positive attributes of superparamagnetic particles seen when applied to cell separation, and FMP eliminate the properties of superparamagnetic particles that impede their utility.

Studies using a Coulter N4 particle analyzer have shown, remarkably, that FMP of diameters from 0.05 to 1.5 micron can be dispersed by vortexing after exposure to a magnetic field (Table). This property was formerly attributed only to superparamagnetic particles.

| Condition | Particle Diameter (micron) |
| --- | --- |
| Pre-magnet | 1.72 |
| Post Magnet-vortex | 1.62 |
| Post Magnet-inversion | 4.96 |

The high magnetic susceptibility of ferromagnetic particles, as compared to superparamagnetic particles, provides rapid magnetic collection on the order of seconds to minutes. Also, because of the magnetic properties of FMP, the procedure does not require elaborate equipment.

Finally, in the field of cell separation a desirable attribute of uncoated, metallic FMP is the almost complete lack of non-specific binding of non-targeted cells. Quantitative recovery of non-targeted cells is possible using FMP. Particles labeled with CD15-antibody were used to deplete greater than 99% of the granulocytes, and a subset of monocytes known to be CD15 positive, from whole blood with quantitative recovery of the non-targeted lymphocytes (see table).

Lack of Binding to Non-Targeted Cells

| | Lymphocytes | Monocytes | Granulocytes |
| --- | --- | --- | --- |
| Whole Blood | 12,694+ | 2665 | 23,230 |
| CD15 depleted | 12,815 (0)* | 2196 (17.5) | 206 (99.1) |

*Percent Depleted

Solid phase microparticles that separate targeted from non-targeted populations on the basis of gravity rather than magnetics have also been described, for example, in U.S. Pat. No. 5,576,185. Currently, particles that are separated based on gravity are relatively dense and large with diameters between the range of approximately 3 to 10 microns. A known feature of these particles is that because of the density difference between particles and cells, end-over-end mixing allows the particles to pass through a substantial portion of the fluid sample in which the particles are used. The particles traverse past the cells of interest and in doing so bind to the targeted cell population without non-specifically binding to non-target cells. This leads to an efficient separation and a high recovery of non-targeted cells. The separation and recovery of non-targeted cells is superior to that found with superparamagnetic selection alone.

These dense particles are designed to settle by gravity both as a mixing manner (discussed above) and as a manner to separate the desired population of cells from the remainder of the cell suspension. In fact, previous descriptions for example as discussed in U.S. Pat. No. 5,576,185, teach away from the use of smaller particles in gravity selection. For example, the disclosure of this patent teaches that superparamagnetic particles are intended to be maintained in suspension in the sample and consequently are designed for very slow or substantial elimination of gravity settling in the sample suspension. Typically, well-coated materials below 150 nm will show no evidence of settling for as long as 6 months and even longer, for example, as discussed in U.S. Pat. No. 5,622,831. Thus, superparamagnetic particles are not applicable for use in gravity selection technology or density difference mixing. Both procedures function optimally at a density difference of at least 2-3 fold between the particles and the target biomaterial when capturing cells and settling by gravity.

Gravity separation addresses several drawbacks inherent in magnetic separation procedures that utilize superparamagnetic particles including non-specific cell loss due to trapping, time of magnetic collection when using colloidal particles, and/or the high magnetic gradients required for collection of colloidal particles.

One area where superparamagnetic particles have not been used is in large scale chromatographic procedures for the purification of proteins and nucleic acids because such magnetic particles are composed of superparamagnetic materials which are not sufficiently magnetic and thus cannot function in large scale (large volume) applications. An example of large scale chromatographic isolations includes but is not limited to Affinity Chromatography.

By the term "Affinity Chromatography" is meant the purification of a biological molecule with respect to the specific binding of that biological molecule due to its chemical structure to a solid phase. With this structure, the biological molecule can reversibly bind to a reactant which has formed a covalent or non-covalent bond with a chromatographic bed material.

Many different types of chromatography are available for the purification of target proteins (recombinant or native)

from different sources. For most proteins, multiple purification methods are needed to purify a target protein to homogeneity. For large-scale bioprocess purifications, certain chromatographic methods are used. These chromatography methods include:

Ion Exchange—separation of proteins by charge differential where chromatography resins are bound with molecules that are positively charged (to bind negatively charged proteins) or negatively charged (to bind positively charged proteins). Every protein has an Isoelectric Point (pI), which can be exploited to separate proteins by making them positively or negatively charged species depending on the pI of the protein. For example, a protein with a pI of 4 will be negatively charged in a buffer of a pH of 7. The protein mixture can be passed through an anion exchange column, and negatively charged proteins are bound to the column (including the target protein). The bound proteins can then be eluted off of the column by either lowering the pH of the buffer passing through the column (removing the charge from the bound proteins) or by eluting with salt containing buffer, which displaces the bound proteins. Ion exchange is normally used as a $1^{st}$ step in protein purification. (1)

Affinity Chromatography—many different types of affinity chromatography are available. Types of affinity chemistries available range from general affinity (e.g. metal affinity) to more specific affinity, such as antibody/antigen, enzyme/substrate (analog), antibody/Protein A/G and receptor/ligand affinity. These methods rely on binding between the affinity matrix and the target protein. Most of the affinity interactions are highly specific for a particular target protein, and as a result, the target protein binding is both specific and tightly bound. Elution of the target protein requires harsh conditions (including low/high pH) to break the affinity interactions. Metal affinity, which utilizes a protein's affinity for specific bivalent metal ions (Cu, Ni, Co, Zn) requires more gentle conditions for elution of the target protein, including pH 6.0 elution, and competitive elution with imidazole. (2)

Affinity chromatography is a preferred choice for large-scale purification protocols, since there is little to no non-specific binding to contaminating proteins. In addition, many recombinant proteins are expressed with either affinity tags (i.e. short specific peptide sequences for use in either metal or antibody affinity purification) or as a fusion protein with the fusion protein used in the affinity purification. After purification, the fusion protein is cleaved from the target protein.

Another purification procedure is High Performance Liquid Chromatography. By the term "High Performance Liquid Chromatography" (HPLC) is meant a form of column chromatography used frequently for the isolation of biological molecules. The sample is forced through a column by liquid at high pressure, which decreases the time the separated components remain on the stationary phase and thus the time they have to spread out within the column, leading to broader peaks. Less time on the column then translates to narrower peaks in the resulting chromatogram and thence to better selectivity and sensitivity.

Purification Process Design

The design of large-scale purification protocols should involve a minimal number of steps, since the recovery of a protein decreases as the number of purification steps increases. Standard purification methods involve pre-purification processes, including $1^{st}$ separating the target protein from the cells expressing the protein. How this is accomplished depends on the expression system used to produce the target protein. Some expression systems express the protein intracellularly, necessitating the removal of the cells from the media, followed by lysing of the cells and subsequent purification of the protein. Other expression systems express the protein into the surrounding media, requiring the total media content to be passed through the initial purification column.

Concentration of the media feed stream containing the target protein is usually performed to lessen the amount of sample that is to be loaded onto the column. This requires time-consuming steps including filtration of the media to remove the cells expressing the protein. In addition, even after the concentration of the media, there is still a large volume that must be passed through the chromatographic support using a High Pressure Liquid Chromatography (HPLC) system (3). After the target protein is bound to the support, the column is washed with buffer to remove weakly bound proteins. Elution of the target protein is then performed, and the protein containing solution is neutralized, concentrated, and stored.

Thus, there is a need in the field of biological molecule separations including large scale chromatoghy for a ferromagnetic particle, as is in the field of cell selection, that exhibits andvantages over current technologies based on solid supports including superparamagnrtic particles. The advantages of FMP over other superparamagnetic particles include: cost, rapid reaction kinetics, rapid separation kinetics based on the ferromagnetic properties of the particles, simplicity of rinsing and adding of reagents, economy of reagents, and lower non-specific adherence. However, to date there has been no way of using ferromagnetic particles or density particles in biological molecule selection, nor have there been ferromagnetic or density particles useful in biological molecule selection. In this regard, while the term "dense particles" was used previously herein in reference to U.S. Pat. No. 5,576,185, for purposes of discussing the invention herein, the term "density particles" will be used. The reason for this, is that although such particles can have a greater density than the fluid in which used so that they separate by gravity, alternatively, such particles can have a relative density less than fluid so that separation occurs by floating or rising in the fluid. In both cases, density particles can be ferromagnetic or non-ferromagnetic as discussed hereafter.

There is also a need in the art for the elimination of the filtration and concentration steps thus enhancing the rate at which target protein(s) can be extracted and purified from a large-scale sample. The use of a particle that can be used within a sample for binding of the target protein, followed by rapid removal of the particle containing the bound protein, would result in rapid pre-process purification steps, which would greatly reduce the time required for purification. A particle that can be used in this manner would greatly reduce the time required for the pre process steps in the purification by eliminating the need to concentrate and filter the feed stream. For this reduction to occur, a particle would be needed that can be used as a chromatographic support in HPLC, be able to be modified so that affinity ligands can be covalently attached, and the particle must be able to mix with the target protein containing media and be separated from the cells and other debris in the protein containing feed stream. Removal of cells and other debris is essential for use in an HPLC system, since the debris can interfere in the operation of the system by building up pressure due to blocking of the flow by the debris. The following invention disclosed herein describes a unique method using unique FMP and or DP for accomplishing this task.

SUMMARY OF THE INVENTION

The invention provides improved methods, apparatus, and compositions for the selection of biological molecules such as proteins and nucleic acids and others as discussed previously. This selection consists, in part, of mixing and separating components. Separation defined for the purposes of this invention includes any mechanism dependent upon the physical properties of the particles involved. For example, this would include the particle's magnetic properties or density. Throughout the application particles used for magnetic separation are referred to as ferromagnetic particles (FMP) while particles used for gravity settling, or rising as in floating, as a separation step are referred to as density particles (DP). The invention provides for an improved selection procedure based on the properties of sufficiently dense or less dense particles. These particles, when coupled to an appropriate binding agent offer a unique advantage over the prior art because of their superior physical properties.

Thus, in one aspect the invention is a plurality of coated density particles containing a plurality of binding agents bound thereto that recognize biological molecules.

In another aspect the invention is a plurality of coated ferromagnetic relatively dense particles containing a plurality of binding agents, bound thereto that recognize biological molecules.

In yet another aspect the invention is a plurality of coated relatively dense particles containing a plurality of binding agents bound thereto that recognize biological molecules.

In yet still another aspect the invention is a plurality of coated relatively buoyant particles containing a plurality of density particles containing a plurality of binding agents bound thereto that recognize biological molecules.

The method embodying the invention herein disclosed can be utilized with a variety of reactions involving binding agents and their corresponding recognition sites. The term "binding agent" as used herein defines various molecule(s), i.e., monoclonal antibodies that detect and react with one or more specific complementary molecule(s). Examples include, but are not limited to, the following specific complementary biological molecular pairs; antibody/antigen, nucleic acid/complementary nucleic acid, lectin/carbohydrate molecule. The term "biological molecule" includes RNA, DNA, protein, glycoproteins, lipids and carbohydrates. These biological molecules interact with the binding agents bound to FMP and/or DP.

In one preferred embodiment of the present invention, ferromagnetic density particles, which are coated and/or have a blocking agent thereon, within a certain diameter size range, will be used to efficiently select specific targeted biological molecules. By "blocking agent" is meant a coating over sites that exhibit non-specific binding to biological molecules, Examples of such agents include but are not limited to bovine serum albumin, fractions of caragean (seaweed extract), polyglycol and nonionic surfactant. Within a given diameter size range and under desired magnetic conditions, ferromagnetic density particles function even though they maintain their magnetic properties upon removal of a magnetic field. Both the method and means provided by the present invention, when performed together with the particles of the invention, are effective for the isolation of specific populations of proteins and nucleic acids. The method, means, and particles of the invention utilize both a mixing manner that takes advantage of the difference in density between the particles and the targeted biological molecules to effectively capture targeted populations, and a separating manner that takes advantage of the magnetic properties of ferromagnetic dense particles to hold rapidly and tightly the targeted populations at the wall of the container, thus permitting effective removal of non-targeted populations without carryover of targeted populations as is seen with colloidal superparamagnetic particles of the prior art.

Thus, in a further aspect the invention involves a method for isolating biological molecules from a fluid sample. The method involves providing a plurality of coated density particles having bound thereto a binding agent which specifically binds to biological molecules in the fluid sample. At least a portion of the sample is mixed with the particles. The particles with the bound biological molecules are separated and substantially completely removed from the sample. By substantially completely removed is meant in excess of at least about 90%, more typically at least about 95%, and often in excess of 99%, depending on the properties of the magnets used.

In a more specific aspect, the particles are ferromagnetic and are separated by magnetic selection.

In a further alternative, the particles are relatively dense as compared to the fluid sample.

In a yet still further alternative, the particles are relatively buoyant as compared to the fluid sample.

To accomplish this selection, in a preferred embodiment of the invention, a plurality of coated ferromagnetic density particles, having a binding agent thereupon, is combined with a fluid sample containing a biological molecule(s) of interest. In this case, the particles are relatively dense compared to the fluid sample. The sample is mixed such that the relatively dense particles traverse back and forth past the biological molecules, binding to those targeted by the binding agents. Following mixing, the sample is placed in a magnetic field that promotes even dispersion of the particles along the vessel wall containing the sample. The separation is followed by removal of the remaining sample. The targeted population can be easily resuspended while still bound to the particles (even though the particles are ferromagnetic). The preferred particle will be in the size range of approximately 0.5 to approximately 2 microns in diameter but can be significantly larger on the order of up to 10 micron as long as the particular biological molecule of interest can be captured by the larger size particle as determined by one skilled in the art and made of ferromagnetic magnetic material such as, but not limited to nickel, cobalt, or iron. A preferable material for ferromagnetic relatively dense particles can be nickel but any particle (metal, alloy, organic compound or combination of metal and organic compound) can be used as long as the particles are ferromagnetic rather than superparamagnetic as required by the invention herein disclosed.

In a second embodiment of the invention, separation is based upon gravity allowing the density particles, which in this case are more dense particles, to settle out of solution. As explained previously, the density particles could also be used in a manner which encompasses buoyancy with use of a less dense particle in the fluid sample. An effect of gravity upon the particles of the invention could also occur through centrifugation procedures known in the art.

A preferable material for selection based on gravity can be any inorganic (metal) or organic material particle that will settle out of solution by the earth's gravitation field, by centrifugation following the mixing step or by buoyancy.

According to the present invention we provide coated dense particles (ferromagnetic and non-magnetic) for the isolation of biological molecules.

The coatings can take various forms and can include, for example, a coating specific to a particular protein. It may also include, for example, a blocking agent at selected uncoated sites to prevent non-specific binding. Thus, the particles can be made with a coating/blocking agent to be molecule specific; molecule generic such as with a coating for a class such as all DNA; and or non-molecule specific but with a blocking agent for specific types of molecules. The coating and antibody or binding agent adsorb or covalently couple. The coatings and blocking agents will be readily known to those of ordinary skill in the art, and examples are provided hereafter setting forth greater detail.

The particles can be used to isolate total DNA, polyA-containing mRNA, specific DNA sequences, proteins, lipids and carbohydrates. In one embodiment, a plurality of dense, relatively heavy particles having the appropriate binding agent bound thereto are mixed with the sample. The dense particles are ferromagnetic dense particles and capture the desired nucleic acid or protein rapidly separating the desired nucleic acid(s)/proteins from the remainder of the reaction mixture. The mixing and magnetic separation or gravity settling of this embodiment ensure high purity of the desired material bound to dense ferromagnetic particles in the pellet.

In another embodiment, the particles are for large scale chromatographic isolations.

In a more specific aspect, the particles are ferromagnetic and are separated by magnetic selection.

In a further alternative, the particles are relatively dense as compared to the fluid sample.

In a yet still further alternative, the particles are relatively buoyant as compared to the fluid sample.

To accomplish this selection, in a preferred embodiment of the invention, a plurality of coated ferromagnetic density particles, having a binding agent thereupon, is combined with a fluid sample containing a biological molecule(s) of interest. In this case, the particles are relatively dense compared to the fluid sample. The sample is mixed such that the relatively dense particles traverse back and forth past the biological molecules such as by end-over-end mixing, binding to those targeted by the binding agents. Following mixing, the sample is placed in a magnetic field that promotes even dispersion of the particles along the vessel wall containing the sample. The separation is followed by removal of the remaining sample. The targeted population can be easily resuspended while still bound to the particles (even though the particles are ferromagnetic). The preferred particle will be in the size range of approximately 0.5 to approximately 2 microns in diameter and made of ferromagnetic magnetic material such as, but not limited to nickel, cobalt, or iron. A preferable material for ferromagnetic relatively dense particles can be nickel but any particle (metal, alloy, organic compound or combination of metal and organic compound) can be used as long as the particles are ferromagnetic rather than superparamagnetic as required by the invention herein disclosed.

In a another embodiment of the invention, separation is based upon gravity allowing the density particles, which in this case are more dense particles, to settle out of solution. As explained previously, the density particles could also be used in a manner which encompasses buoyancy with use of a less dense particle in the fluid sample. An effect of gravity upon the particles of the invention could also occur through centrifugation procedures known in the art.

A preferable material for selection based on gravity can be any inorganic (metal) or organic material particle that will settle out of solution by the earth's gravitation field, by centrifugation following the mixing step or by buoyancy.

According to the present invention we provide coated dense particles (ferromagnetic and non-magnetic) for the isolation of biological molecules.

For chromatographic isolations, preferably particle sizes of greater than about 2 micron to about 10 micron are used when separation is primarily through gravity settling. But any one trained in the art will appreciate that any particle greater than 10 micron and sufficiently dense is anticipated by the invention. Although gravity settling is indicated, magnetic or buoyancy separation will also work. While preferred sizes for the particles are given, any particle size that settles by gravity in about 5 to about 15 minutes is acceptable. Typically, such particles are those from about 500 mm to about 10 micron or larger, more typically about 2 to about 10 micron.

The invention as herein described lends itself to automation. Both the mixing and magnetic separation and gravity separation steps of the invention can be easily automated. Automation is a necessary requirement for ultimate commercialization of the technology for diagnostic applications.

DETAILED DESCRIPTION OF THE PREFERRED EMBODIMENTS

According to preferred embodiments the present invention encompasses methods, apparatus, and particle compositions for rapid and efficient selection of target biological molecules in a fluid sample.

The disclosed invention has particular utility in various laboratory, diagnostic and clinical procedures involving bio-affinity reactions. In such procedures, particles are used which are, preferably relatively dense and could be magnetically responsive compared to the targeted biomaterial. Further, the particles constitute a binding agent capable of binding the biological molecule of interest in the test sample. In the disclosed invention, a particle-target complex is formed between the ferromagnetic dense particle and targeted biological molecules after the binding agent recognizes the biological molecules. The selection of the biological molecules is accomplished through efficient mixing and separation.

Figure 1:
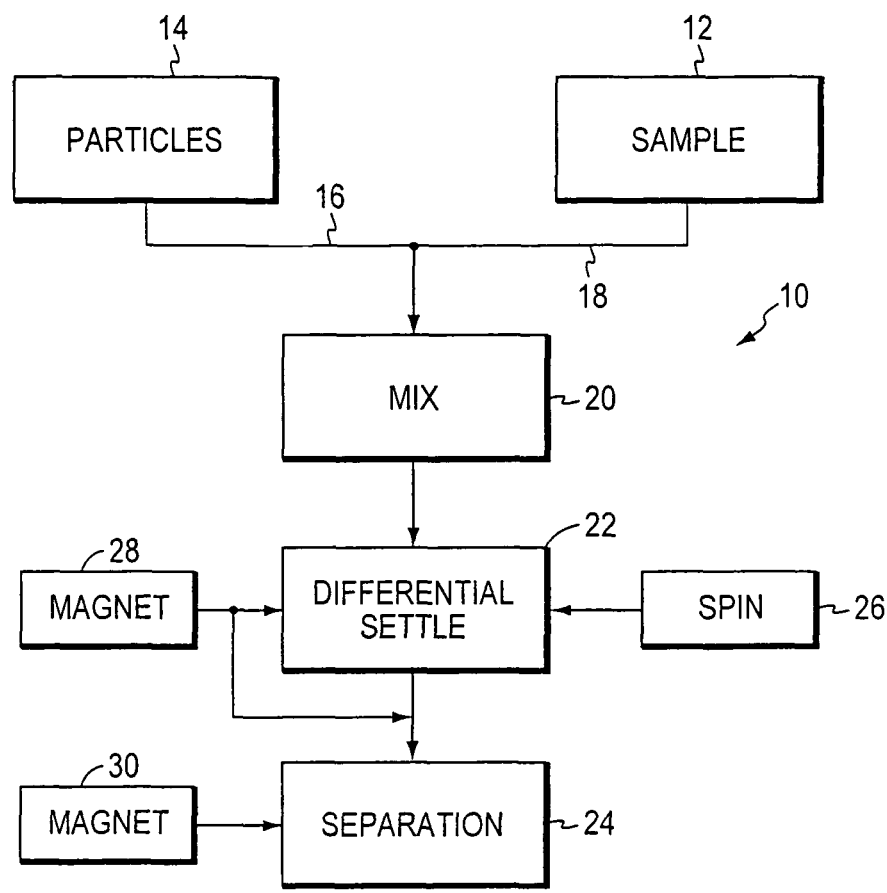
FIG. 1 is a schematic block diagram of one embodiment of selection with density particles.

As shown in FIG. 1, one embodiment of the method and apparatus according to the invention is designated generally by reference numeral 10. The apparatus 10 includes a fluid sample 12 containing a biological molecule as described below. The apparatus 10 also includes a source of dense particles 14 as manufactured and described below. The particles 14 include a binding agent, which is able to bind specifically to a target biological molecule. The binding agent is bound to the particles 14 by any method known in the art. The particles 14 are combined through lines 16 and 18 with at least a portion of the fluid sample 12 in a mixing stage 20. Depending on the volume, the mixing stage 20 is either end-over-end nutation or vortexing. Alternatively, the mixing could be achieved with a mixing packet. The combination is allowed to form particle-target biological molecule complexes.

Once the particles 14 have been mixed with the fluid sample 12, they are allowed to differentially settle by gravity sedimentation as shown by block 22.

The apparatus 10 can be an automatic device to combine the fluid sample 12 and the particles 14, and then move them between the stages. Also, the apparatus 10 can be manual where an operator uses a test tube or similar container through the mixing stage 20, settling stage 22, and separating stage 24, While the settling and separation steps 22 and 24 can preferably be accomplished by gravity separation alone, additional steps may be included where desired. The sample 12 and the particles can be briefly spun, illustrated by block 26, to accelerate the settling step 22. The particles 14 can also be of ferromagnetic materials. With the ferromagnetic particles 14, a magnet or magnetic field, illustrated by block 28, can be applied to the bottom of the container (not illustrated) to accelerate the settling step 22. Additionally, the magnetic field 28 can be maintained or can be applied to the bottom of the container to ensure that the particles 14 are not removed and can be passed by or through a magnetic field caused by magnet 30 to insure that no particle fragments or particles 14 remain in the fluid sample, such as when the sample is to be reinserted into a living organism, such as a human body.

Figure 2:
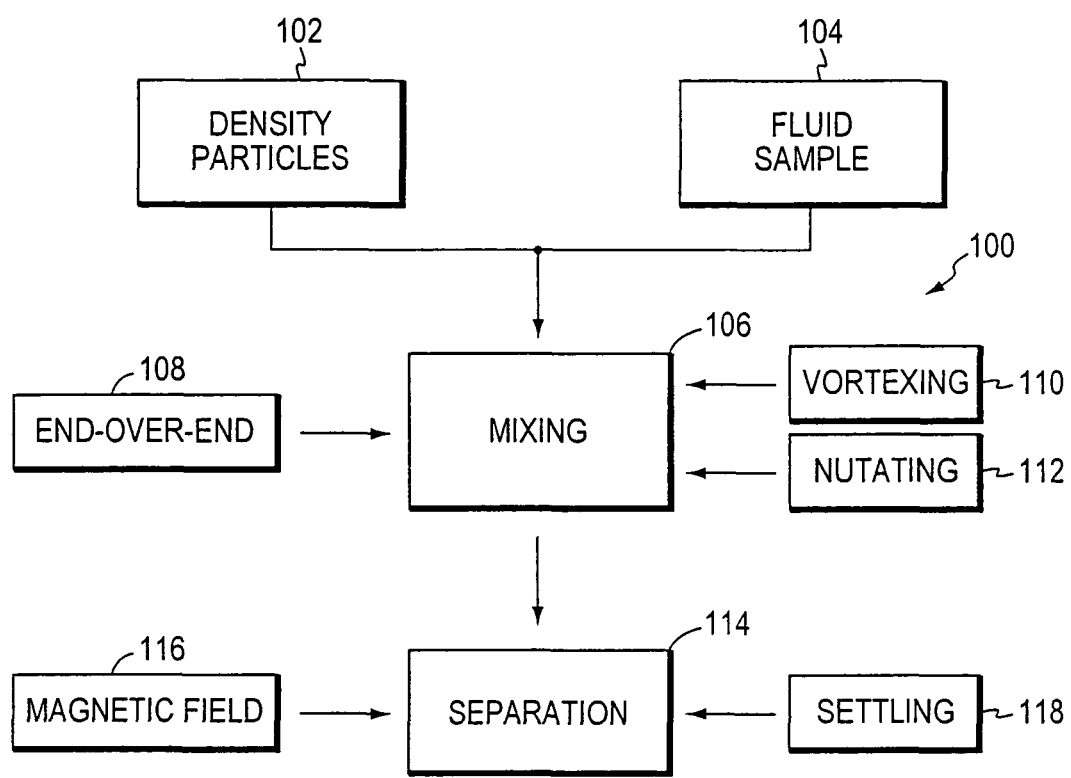
FIG. 2 is a schematic block diagram and another embodiment of selection with density particles.

As shown in FIG. 2, another embodiment of the method and apparatus of the invention is depicted in a block diagram 100. The apparatus includes a fluid sample 104 and a source of density particles 102. The particles 102 include a binding agent, coating or blocking agent for binding specifically to a target population. The binding agent, coating or blocking agent is bound to the particles 102 by any means known to those of ordinary skill in the art. The particles 102 are combined with at least a portion of the fluid sample 104 in a mixing stage 106. Depending on the volume, the mixing stage 106 is either end-over-end 108, vortexing 110 or nutation 112. The combination is allowed to form particle-target complexes where, together with any particles not forming complexes, are separated by either settling 118 for both density particles (dense particles) or DP, or through a magnetic field for FMP 116.

The apparatus 100 can be an automatic device to combine the fluid sample 104 and the particles 102, and then move them between the stages. Also, the apparatus 100 can be manual where an operator uses a test tube or similar container through the mixing 106, separating 114, settling 118, or magnetically induced movement 116. Finally, the apparatus can be in a semi-automated fashion, using a combination of automated and manual use.

Although described with respect to its use with relatively dense particles, it will be readily apparent to those of ordinary skill in the art that, apparatus 10 can be easily modified to work with density particles, as previously defined, which include those which are relatively less dense and "float" after mixing.

There are two principle embodiments for the methods portion of the invention that differ only in the separation component of the selection process. While both require efficient particle mixing, in a particularly preferred embodiment a magnetic field is utilized to separate targeted material from the fluid sample. A further embodiment utilizes the density difference between an individual particle of the invention and its target to perform a separation in the fluid sample of non-target components. For example, separation could be the result of a gravitational effect or buoyancy. In yet still further form, both magnetic separation and separation based on gravity or based on buoyancy could be combined in a system such as that shown in FIG. 2.

Reactions as described above can be employed in testing biological samples for the determination of a wide range of target biological molecules, representative of which are nucleic acids, both RNA and DNA, and proteins, both high and low molecular weight proteins as well as peptides.

For biological molecule selection, the fluid sample can be, for example, a biological fluid including whole blood or a portion thereof, bone marrow, leukopheresis product, spinal fluid, urine, plasma, serum or other body fluids containing the biological molecule(s) of interest such as described above and as can be conceived by one skilled in the art.

To operate in accordance with a particularly preferred embodiment of the invention, the particle must be ferromagnetic, dense and the metallic surface must be coated and perhaps include a blocking agent as previously discussed, as it is known in the art that metal/metal oxides bind non-specifically to RNA, DNA and proteins. Without coating and/or blocking agents the specificity provided by the binding agent would not exist as the uncoated particle would bind both the specific biological molecule of interest and all other biological molecules as well.

On the other hand, it may be desirable to have a metal uncoated which is specific to a generic class of molecules, for example, all DNA, but not other biological molecules in a sample.

The particles preferably have an irregular surface (not smooth). On the other hand, uniform particles of the appropriate density with a smooth surface are also anticipated by the invention for the specific applications. The metal or metal oxide surface may be derivitized with additional metals, metal oxide, molecules, or polymers to aid in the adhesion of the probe, minimize non-specific binding, protect the primary particle from oxidation, and/or modify the solution behavior. Coating of the particles is done by means known in the art. The specification requires a coating that minimizes non-specific binding of biological molecules. In the case of DNA or RNA, slightly negatively charged surfaces, i.e. carboxyl coated surfaces would minimize non-specific binding of negatively charged nucleic acids.

The attachment of probes to the coated ferromagnetic particles (FMP) or density particles (DP) particles may be by adsorbtion, direct chemical bonding or through affinity binding i.e. biotin-streptavidin. In this context, it will be appreciated that when referring to ferromagnetic particles (FMP), that they are also density particles (DP) as defined, but are referred to as FMP to reflect their magnetic properties. FMP are coated with a polymer that contains chemical moieties available for covalent attachment to specific probes. One such particle has a silane coating with amino groups available to covalently couple to the biological molecules via appropriate linkers. The chemical functional groups may also include those known in the art such as, but not limited to, hydroxyl, carboxyl, aldehyde or sulfhydryl. Using coated particles non-specific binding of unwanted biological molecules is significantly reduced and in some cases is eliminated.

Silanes can be used to adhere DNA probes but in fact these are not as desirable as some of the polymer linkers. Specifically, silanes often do not permit proper orientation and the non-discriminant binding of probes does not permit optimum hybridization efficiency. The silane can be supplemented with a blocking agent such as BSA, for example on bare spots on the particles, which serves to block certain specific molecules which would otherwise bind to silane from binding to the particles. Silane can be used in conjunction with other molecules to make films for DNA hybridization. However, dilutions of surface molecules with those containing functional groups used for binding of oligo's and molecules with hydrophilic groups to optimize solvent compatibility represent surfaces optimized hybridization efficiency, and minimal non-specific binding.

FMP surfaces consist primarily of bridged metal oxide and hydroxyl moieties. As such, these surfaces are readily amenable to treatment via organosilane coupling described below. These surfaces can be derivitized with functional polymeric species containing a negatively charged surface affinic group such as a carboxyl or phosphate (i.e. modified polyethylene glycols and polylactic acids). Subsequent modification would result by utilizing linking chemistry known to those of ordinary skill in the art, for example, zero length crosslinkers such as dimethylaminopropyl)-carbodiimide (EDC) or n-hydroysuccinimide (NHS). These groups form an amide linkage with available amine groups pendent on proteins from amino acids (i.e. lysine) or terminal amines on DNA or RNA via synthetic conjugation techniques.

Bifunctional molecules, i.e., those containing two identical or non-identical functional groups can be used to covalently attach proteins, polymers, DNA, or RNA to the surface. These include the natural amino acids, aminopropionic acid, thioglycolic acid and similar like substances. Also, included are denatured and/or fragmented biomolecules, for example, bovine serum albumin and sub-fractions of bovine serum albumin as isolated by HPLC or similar chromatography technique.

The preferred method of coating is by direct absorption from an aqueous solution of coating molecule and FMP's. Approximately 1 g. of FMP is diluted with 100 parts distilled water by weight. A solution containing 1 to 10 parts of dissolved linker is added under rapid agitation and allowed to mix for a period of time. Several washes via settling and decantation are necessary to remove unbound linker.

Specifically, 100 ml. of distilled water is added to 1 g. of FMP and sonicated using an ultrasonicator. Separately, 0.2 g. of polylactic acid (m.w. 20 KD) is dissolved into 10 ml. of distilled water. The two are combined and vortexed for 5 minutes. After FMP settling approximately 95 ml. of water is removed and replaced with clean distilled water. The process is repeated 3 times to remove unbound polylactic acid. The resulting FMP are now modified with surface polymeric acid groups that can be further modified via EDC coupling.

Furthermore, dextrans may be used to modify the surface of FMP's. Dextrans can be used for immobilization of proteins and other biomolecules. Modified dextrans with extensive carboxyl or amine group attachment are of particular importance due to their affinity to the FMP surface. Modified dextrans are conjugated to the FMP surface by first dispersing the FMP in distilled water from 1 to 10 percent solids concentration through ultrasonication or vortexing. An amount of dextran between 0.5 and 10 weight percent is added to the agitated particle suspension and allowed to incubate. Several settling or magnetic separation steps are required to decant the excess dextran. The liquid can be replaced with distilled water or buffer.

Where biotin-streptavidin coupling is preferred, strepavidin can be bound to the particles via covalent or non-covalent attachment, and the biotynylated probes can be, synthesized using biotynylated nucleotides as described in the art (Langer).

Under some acidic conditions the nickel oxide coating may be deleteriously affected. To avoid such effects, an additional inert metal oxide coating is beneficial in preventing degradation of the particle and to permit processing. Such a coating may consist of silica or titanium oxide coatings, but other metal oxides are possible including zinc and zirconium.

The nickel FMP surface can be passivated or protected from chemical attack by coating with a dense layer of inert metal oxide, preferably silica or titanium oxides. Oxide surfaces can be formed from aqueous precipitation of sodium silicate or titanium oxychloride or similar, or in an organic medium from a sol-gel precursor such as tetraethylorthosilicate.

The nickel surfaces can be coated directly with a protective layer of silica oxide by dispersing 1 g. Nickel particles in 100 ml. of distilled water adjusted to pH=10 by addition of 0.1M NaOH and adding 1.5 ml. of sodium silicate solution (28% silicate) under agitation. The solution is readjusted to pH=10 by addition of 0.1M phosphoric acid. Stirring is continued for 24-hours. The remaining sodium silicate can be precipitated onto the particle surface by addition of 4 volume equivalents of ethanol, or reduction of the pH to 7 with 0.1M phosphoric acid. The silica derivitized particles are purified by repeated settling or magnetic separation steps followed by decantation and resuspension in distilled water or buffer.

To increase the silica shell thickness or as an alternative primary coating system for the nickel FMP's, sol-gel chemistry can be utilized. Particles are dispersed in ethanol via vortexing or other vigorous agitation and an inorganic precursor is added and hydrolyzed with ammonia. Specifically, 1 gram of Nickel FMP which is silica coated is dispersed in 300 ml. ethanol. 1 ml. tetraethylorthosilicate is added and 4 ml. of 2-M ammonia dissolved in methanol is added under gentle agitation. The suspension is agitated for 24 hours. The tetraethylorthosilicate and ammonia additions can be repeated until a desired shell thickness is achieved. The silica derivitized particles are purified by repeated settling or magnetic separation steps, followed by decantation and resuspension of FMP's in distilled water or buffer.

Analagous coating methods known to those of ordinary skill in the art can be performed to derivitize the surface of other nickel or other ferromagnetic or density particles with titanium oxide or zirconium oxide. The organosilane methodology stated above can be used to functionalize the metal oxide surface. A properly coated FMP should behave identically to untreated particles in settling and magnetic collection.

In addition, for operation in accordance with a particularly preferred embodiment of the invention, the particles are ferromagnetic and sufficiently dense to ensure proper mixing. For example, iron, cobalt, nickel (and various alloys of these metals) are typical ferromagnetic dense particles. As previously noted, "dense particles" are density particles that have a relatively high density as compared to a fluid in which they are used to achieve sufficient mixing and subsequent separation, for example, by gravity. Ferromagnetic dense particles are metals, which can be permanently magnetized upon application of an external magnetic field. This external field is typically applied by another permanent magnet or electromagnet. Metallic particles greater than about 30 nm in diameter typically are considered ferromagnetic. Thus, the lower limit particle size can be in the range of about 50 nm in diameter. The upper limit in particle diameter is defined operationally as that particle diameter above which the ferromagnetic dense particles cannot be dispersed by simple mixing after having been placed in a magnetic field. Preferably, this upper limit is in the diameter size range of approximately 2.0 microns. Thus, the FMP that are operable in the invention can range in size from approximately 50 m in diameter to approximately 2,000 nm in diameter, with a more preferred diameter in the range of from about 200 nm-to about 1,500 nm and a most preferred size range of from about 400 nm-to about 1,000 nm (about 0.4-about 1.0 microns). It will be further appreciated that the density of the particle must be sufficiently different than that of the target biomaterial such that the particles traverse past the target biological molecules during mixing, thus leading to binding of the target population.

According to the present invention, and as will be readily appreciated by those skilled in the art, the volumes of the fluid sample can vary depending on the procedure being performed. For research and diagnostic applications, a volume as little as ten microliters can be utilized while for some diagnostic applications and clinical applications the volumes can range from typically around 1 ml up to several liters. A particularly advantageous feature of the invention is that both diluted/processed (centrifugation; gradient centrifugation; gravity) and undiluted samples can be processed. The sample (diluted or undiluted) is simply added to the particles or the particles are added to the sample for applications such as, but not limited to, isolation of mRNA, DNA, proteins and samples for processing in mass spectrometry analysis.

Due to the above described density differences, in the practice of the invention mixing causes the particles to traverse gently past the target biological molecules and bind efficiently to recognition sites.

One such process, but not limited to such a process, is end-over-end mixing. End-over-end mixing is appropriate for volumes greater than 0.5 ml, but can be easily performed for smaller volumes. The mixing vessel can be totally full of liquid, which minimizes sloshing, or the vessel can be partially full which permits sloshing. A test tube holder that rotates end-over-end at speeds from about 5 revolutions per minute to about 60 revolutions per minute is generally preferred. For volumes at least 10 ul, mixing can be accomplished by vortexing or nutation with a preferred volume of about 0.2 to 0.5 ml. Vortexing with larger volumes can be possible, as any mixing process that promotes movement of particles relative to target biological molecules falls within the scope of the invention. Mixing times can vary depending on the mixing process. For small volumes, mixing times on the order of seconds to minutes are appropriate; while for larger volumes mixing times range from about 1 to 20 minutes or longer. It will be appreciated that mixing times can be outside the preferred range and still fall within the scope of the invention.

The mixing times of the present invention are very rapid, on the order of seconds to a few minutes. The density of FMP is such that during mixing by gravity (end-over-end) or enhanced gravity (nutation) particles contact the desired biological molecules in solution at rates greater than by classical diffusion thus leading to the need for significantly fewer particles than used in the art. This results in a more cost-effective reagent and significantly lower non-specific binding due to the lower surface area.

Magnets appropriate for capture of targeted biological molecules bound to particles have been described in the prior art literature, such as in U.S. Pat. No. 5,186,827. In a particularly preferred embodiment of the present invention, the magnetic field generating source can constitute sets of from 2 to 8 permanent magnets or electromagnets. The magnets are arranged so as to define a cavity, which accommodates the container. In this embodiment, the polarity and positioning of the magnets located on the opposite sides of the cavity are such as to produce flux lines, which generate a high gradient magnetic field within the test medium container and expose the sample fluid to the magnetic field. The magnets can be housed in a ferromagnetic yoke which serves to enhance the field strength produced by the apparatus.

By controlling the quantity of magnetic particles added to the test medium, relative to the exposed surface area of the wall of the container in contact with the test medium, and controlling the orientation of such exposed surface so as to be substantially coextensive with the flux lines of the magnetic field, it is possible to cause the magnetic particles to adhere along the exposed surface of the container wall in essentially a single layer. By operating in this way, occlusion of nonspecifically bound substances, such as non-targeted biological molecules, in the immobilized magnetic particles is virtually negligible. Besides the preferred embodiment discussed above, any magnetic configuration that attracts the particles to the vessel wall without leading to non-specific trapping of non-targeted biological molecules falls within the scope of the invention.

Magnetic separation times vary depending on the sample volume and range from approximately around three seconds up to about five to about ten minutes. It is to be noted that a significant advantage of the present invention, which utilizes ferromagnetic dense particles, over selection technologies based on superparamagnetic particles, is that very short magnetic capture times are possible. This results in a very rapid selection process that is compatible with the high throughput screening technologies that have evolved in recent years. The ferromagnetic particles described herein will result in a significant improvement in throughput time compared to that seen with superparamagnetic particles.

Though any ferromagnetic dense particle in the desired size range will work in the invention, a particular method for making suitable particles is described below. Methods for making metallic particles are well known in the art (see for example Zach, M. P., Penner, R. M., Adv. Mat., 2000, 12:878).

Example 1

Synthesis of ferromagnetic dense particles containing nickel:
1. Weigh out 4.0 gm sodium hydroxide and dissolve completely in 100 ml beaker by stirring while beaker is covered with parafilm.
2. Weigh out 2.04 gm nickel chloride and dissolve in 100 ml distilled water in a 200 ml beaker.
3. Pour 200 ml distilled water into a clean reaction vessel at room temperature.
4. After nickel chloride solution has mixed for 20 minutes, examine to determine if any debris is floating on the surface of the solution. If debris is present, decant fluid leaving debris behind.
5. Measure out 14 ml triethanolamine. Under a hood, add triethanolamine to the nickel chloride solution. Observe an expected color change to aqua green.
6. Measure 38.5 ml of hydrazine.
7. Add the sodium hydroxide solution to the nickel chloride-triethanolamine solution while continuing stirring on a magnetic stirrer. Observe a color change to a dark pea green color.
8. After complete mixing pour the nickel chloride-triethanolamine solution, through the funnel into a reaction vessel. The reaction vessel contains a lid that has a port for adding materials. The port is capped during the reaction. Also, a condenser is attached to the lid and vented to the outside. The condenser has room temperature water passing through it. The production of particles takes place in a chemical hood.

9. Add measured hydrazine to the reaction vessel. Remove funnel and cap with a plug.
10. Increase heat to 105.degree. C. and stir.
11. Observe reaction vessel to ensure that reaction is not occurring too violently. If foam is rising too high into the condenser add approximately 200 ul of butyl alcohol to reduce foaming.
12. Once the reaction has occurred—at approximately 105.degree. C.—the solution in the reaction vessel will change from green to black.
13. Allow reaction to proceed to completion (around 2.5 hrs).
14. Verify the reaction is complete by checking for the presence of excess hydrazine. Turn off stirrer and determine whether level of foaming rises or not. If level rises resume stirring to speed continue to burn off excess hydrazine. If level does not rise the reaction is complete.
15. When reaction is complete, turn off heat and continue stirring to speed up cooling.
16. Decant supernatant from particles and save for neutralization.
17. Rinse and suspend particles in distilled water.
18. Rinse 6 times as in 17.
19. Place final particle pellet in beaker covered with aluminum foil and place in oven at 250.degree. C. for 48-72 hours.
20. Remove beaker from oven and allow particles to cool.

A second embodiment of the invention utilizes the settling ability of the particles of the invention to separate the target biological molecules from the fluid sample. Settling for purposes of this invention is defined as a separation of the particles of the invention away from a substantial portion of the fluid sample because of an unequal effect of an independent or outside force upon the particle-target complex and the rest of the sample. For example, either gravity or the buoyancy of the particles will cause settling from the fluid sample. Within this embodiment, the particles of the invention also include non-ferromagnetic dense particles. Gravity settling with these particles of the invention allows for the capture of targeted biological molecules.

Centrifugation, also included as a mode for settling, can be used to separate the particles of the invention following proper mixing. The particles of the invention have an advantage of providing rapid and efficient mixing with relatively low time and speeds of centrifugation for separation of target populations.

The method of isolating biological molecules with the particles described herein is described hereinafter in general terms. For the isolation of each biological molecule it will be appreciated by practitioners in the art that volumes, mixing, separtion times and particle diameter may vary and specific experiments need to be performed to determine optimal conditions for each bilogical molecule.

Equipment required for optimal performance FMP/DP:
1. Mixer: Due to the density difference between FMP/DP and biological molecules (~8 fold), proper mixing is desired to ensure contact between the particles and the targeted cells. For some applications where speed is not essential, particles may not need to be continuously mixed.

For reaction volumes≤to 0.5 ml mixing can be accomplished by vortexing at a low speed using a Vortex Genie 2 that has variable speed control. A Vortex Genie 2 with a timer is desirable but a timer is not essential.

For volumes≥0.5 ml up to 50 ml mixing can be accomplished by end-over-end mixing using an ATR Rotamix mixer with variable speed. Recommended mixing speed is 15-30 rpm, but must be optimized for each application.

2. Magnetic Separation:

Ideal magnets that can be used with FMP described herein can be obtained from Dexter. Magnets. Different magnets are available for sample volumes from ≤0.5 mL to 50 mL, or larger on a custom basis Magnets from suppliers of superparamagnetic particles (Dynal Biotech, Stem Cell Technologies, Inc.) will also work with FMP.

3. Demagnetizer:

To ensure well dispersed particles, it is recommended, but not required unless particles inadvertently come in contact with a magnetic field prior to use, that the particles be demagnetized immediately prior to the addition to the sample, using a demagnetizer/degausser such as that commercially available from Data-Link Associates.

Hold the demagnetizer at the bottom of the test tube containing the particles; (hold test tube in one hand; demagnetizer in the other hand; demagnetizer can touch test tube); turn unit on by holding "on button" in the on position; rotate demagnetizer in a clockwise or counterclockwise motion for 10-12 seconds; While unit is still on (if unit is turned off before this step particles will be magnetized) slowly move the demagnetizer away from the test tube (about 3 feet; arms length); turn off demagnetizer.

Preparation of Particles Prior to use in a Specific Experiment:

Particles should be rinsed prior to use. FMP can be rinsed in three different ways because of the nature of the particles. Step 1 or Step 2 is recommended. To save time, rinsing with magnetic separation is possible but the particles should be demagnetized prior to use. Rinsing buffer is Phosphate Buffered Saline/0.1% BSA/pH 7.2. Final resuspension buffer can be PBS/BSA buffer or specific buffers used for the specific isolation of a given biological molecule.

1. Centrifugation: Centrifuge at 500 rpm for 5 minutes. Following centrifugation, remove buffer, add new buffer and resuspend particles by vortexing or pipette up and down. Repeat two times. Resuspend to original volume using your working buffer (i.e. PBS/BSA).

2. Gravity Settling: Allow particles to settle by gravity for 2-3 minutes. Following settling, remove buffer, add new buffer and resuspend particles by vortexing or pipette up and down. Repeat two times. Resuspend to original volume using your working buffer (i.e. PBS/BSA).

3. Magnetic Separation: Place particles in magnetic separator for 4-5 seconds. Following magnetic separation, remove buffer, remove test tube from Magnetic separator, add buffer and resuspend by vortexing or pipette up and down. Repeat two times. Resuspend to original volume using working buffer (i.e. PBS/BSA or specific buffer needed for isolation of a specific biomolecule). Demagnetize the final particle suspension.

Generic Method-Magnetic Separation

The method for the selection of biological molecules is extremely user-friendly, rapid and can be performed with, but not limited to, diluted and undiluted whole blood, bone marrow, spinal fluid, serum, plasma, urine and cell homogenates.

1. Rinse FMP prior to use by one of the rinsing procedures.
2. Add FMP directly to the sample or sample directly to FMP with or without removal of rinsing buffer.
3. Mix either by vortexing, nutation or end-over-end mixing.
4. Immediately place in a magnetic separator.
5. Carefully remove sample while in the magnetic field to obtain sample depleted of the specific biological molecule(s). The magnetic pellet is a source of the specific targeted biological molecule(s).

Generic Method-Settling

The method for the selection of biological molecules is extremely user-friendly, rapid and can be performed with, but not limited to, diluted and undiluted whole blood, bone marrow, spinal fluid, serum, plasma, urine and cell homogenates.

6. Rinse DP prior to use by one of the rinsing procedures.
7. Add DP directly to the sample or sample directly to particles with or without removal of rinsing buffer.
8. Mix either by vortexing, nutation or end-over-end mixing.
9. Immediately stand the sample vessel upright and allow DP to settle (5-8 minutes).
10. Carefully remove sample to obtain sample depleted of the specific biological molecule(s). The pellet is a source of the specific targeted biological molecule(s).

FMP/DP coupled to binding agents that recognize specific biological molecules according to the invention may be used in the art in a wide range of procedures/applications. For example purposes only, a number of potential applications are listed below. The binding reaction is identical for each type of particle while for FMP the separation step is based on magnetics and for DP the separation step is based on gravity settling or alternatively, flotation.

Immunoprecipitation of Proteins

FMP or DP coupled to Protein A or Protein G will be used for the small scale immunoprecipitation of proteins. For immunoprecipitation, the target protein is bound by a specific antibody. FMP or DP-Protein A or FMP or DP-Protein G then can bind to the Fc region of the specific antibody so that the immune complex is labeled with either FMP or DP depending whether gravity settling or magnets is used in the separation step.

Purification of Proteins

Large scale purification of proteins is currently preformed by chromatography procedures primarily based on column chromatography and dependent on properties of the proteins being isolated i.e. molecular weight and charge. Proteins are also purified by bioaffinity column chromatography where a specific binding agent that recognizes the biological molecule of interest is immobilized on particles that are present in the column. During chromatography the sample flows through the column and the protein of interest binds to the immobilized binding agent. The column is then rinsed free of non-targeted biological molecules.

Bioaffinity column chromatography is expensive and relatively slow. The use of FMP or DP in place of a column should result in significantly faster separations that exhibit less non-specific binding/trapping of non-targeted biological molecules. Use of solid phase particles described herein should also be more cost effective than current chromatography procedures used to purify proteins.

The appropriate particle with the specific binding agent bound thereto i.e. an antibody specific to the protein of interest is simply added to the sample containing the protein of interest and mixed manually or in an automated instrument (FIG. 1 or FIG. 2) as described. Using FMP, as an example, the sample vessel is then placed in a magnetic field that preferably distributes the particles around the inside wall of the entire vessel thus minimizing non-specific trapping of non-targeted proteins and other biological molecules. The non-targeted proteins remaining in the sample fluid are easily removed by decantation or by flow. The purified protein bound to FMP can be resuspended, concentrated, using an appropriate magnetic configuration that collects the FMP in a single area in the sample vessel, and removed from the FMP using means known in the art. Highly purified proteins can be obtained in a rapid cost effective manner.

Another significant advantage of the methods disclosed herein for protein purification is that the starting material often contains cell debris and other junk that would clog chromatography columns but FMP/DP would not be affected. Thus, pre-preparation steps that are necessary for column chromatography procedures may not be necessary when using FMP/DP.

Rapid Change of Buffer Conditions

There are numerous situations in biological research where buffer conditions need to be changed i.e. in sample preparation for mass spectrometry. If the analyte of interest i.e. protein fragment, protein, peptide is immobilized on FMP it is very easy to change buffer conditions. The sample, containing FMP bound to the biological molecule(s) of interest in a buffer i.e. Buffer A, is simply placed in a magnetic field. Buffer A is removed by decantation or flow either manually or in an automated apparatus and FMP are resuspended in the new buffer conditions i.e. buffer B.

Immunoassays

Immunoassays are routinely performed in research and clinical diagnostics to determine the presence of biological molecules, usually proteins or small organic molecules, e.g. drugs or drug metabolites in a fluid sample. The fluid sample used in standard immunoassays is either serum or plasma. Thus, prior to performing a standard immunoassay, serum or plasma must be prepared from a whole blood sample usually by centrifugation. The format for these assays is often micotitre plates where the sample volume is limited to around 200 ul.

Two unique features of density particle technology should offer a significant advantage over current immunoassay technology. First, since density particles work in undiluted whole blood, whole blood would be the sample of choice thus eliminating the time required to prepare either a serum or plasma sample. Second, since sample volume isn't limited to 200 ul a significant increase in assay sensitivity should be realized with density particle technology. For instance, sufficient density particles could be added to 10 ml of whole blood thus capturing the biological molecule of interest from 10,000 ul rather than the 200 ul seen in routine immunoassays. This represents a potential 50 fold increase in the amount of the biological molecule of interest which should lead to a 50 fold increase in sensitivity. Such an increase in sensitivity is extremely important when the biological molecule of interest is present in very low amounts as is often seen in the art.

The following example describes use of density particles.

Nucleic Acids

Example I

This example addresses purification of mRNA from crude extracts of human and animal tissues, plants or cells.

mRNA is susceptible to degradation by RNase present in cell lysates, which causes difficulty in obtaining a reasonable quantity of good quality mRNA by conventional methods as is well known in the art. Shortening the time of the mRNA purification procedure is a key factor in preventing such degradation. The invention described herein provides a more rapid means for purifying mRNA.

The mRNA can potentially be purified by the use of FMP coupled to oligo poly-dT (oligo (dT)25). Cells are lysed by 1% LiDS (lysis buffer: 100 mM Tris-HCl, pH 8.0, 500 mM LiCl, 10 mM EDTA, pH 8.0, 1% LiDS, 5 mM dithiothreitol [DTT]). The cell lysate is added directly to pre-washed FMP, the pellet is resuspended and nutated or vortexed or mixed end-over-end. It will be readily apparent to one of ordinary skill in the art that the mixing time needs to be determined as appropriate for the specific sample. At the end of the mixing period, the reaction tube is placed in a magnetic field and the FMP are allowed to collect for 1-2 minutes depending on the reaction volume. The supernatant is removed and the pellet is washed with washing buffer (10 mM Tris-HCl, pH 8.0, 150 mM LiCl and 1 mM EDTA) by the rinsing technique detailed above. The mRNA can be eluted with elution buffer (10 mM Tris-HCl, pH 8.0) from FMP at high temperature, e.g. 65° C.

Example II

This example describes construction of a cDNA library for human and animal tissues, plants or cells.

This is an extension of the mRNA purification procedure. The captured pure, intact poly(A)+ mRNA on FMP (as a solid phase) is used as a template to synthesize their complementary cDNA by using oligo $(dT)_{25}$ as a primer for reverse transcriptase. As a consequence the first strand cDNA library covalently linked onto FMP can be repeatedly used for specific applications like cDNA amplification, cDNA cloning and subtractive hybridization.

Example III

This example describes Subtractive cDNA cloning.

Subtractive cDNA cloning is a powerful tool used to isolate genes which are specifically expressed in a particular cell type or tissue, at a specific time or in response to a particular drug or reagent. Common transcripts between two samples (target vs. subtractor) are subtracted away, leaving the specific transcripts (mRNA) in the solution for further analysis.

mRNA is purified from target and subtractor cells, respectively, by using FMP conjugated with poly(dT)25 as stated previously. The target mRNA is eluted from the particles by means known in the art. The complementary cDNA to subtractor cell mRNA is synthesized by reverse transcriptase using (dT)25 as primer. The subtractor cDNA coupled on FMP is isolated by denaturing the cDNA/mRNA complex. After washing, the subtractor cDNA on FMP is hybridized with eluted target mRNA, leaving unhybridized target mRNA in solution. The unhybridized target mRNA is collected and converted into cDNA and subcloned into a vector for further identification.

Example IV

This example describes purification of single strand DNA (ss DNA).

FMP can be used to isolate any single strand DNA from different sources, e.g. virus, phage or phagemid, and even genomic DNA in a way similar to mRNA. An oligonucleotide complementary to a segment of target ssDNA is covalently coupled to FMP as described above. Alternatively, the oligonucleotide is chemically biotinylated, which can be captured by streptavidin-coated FMP. Therefore, the ssDNA target can be selectively isolated from crude materials by either direct hybridization with the oligonucleotide-coupled FMP or indirectly by hybridization with biotinylated oligonucleotide following capture with streptavidin-coated FMP. After washing, the captured ssDNA can be released by denaturing (heating, alkaline etc.). Such purified ssDNA should be ready for other applications, e.g. in vitro mutagenesis (Promega's altered sites II in vitro mutagenesis systems). Where the DNA is present in a sample in double stranded form as in a cell lysate, a strand separation step is initially required.

Example V

This Example describes selective cloning of a specific gene from cDNA library

The cDNA library is amplified in bacteria and purified by standard methods. Single strand cDNA are prepared by using phage F1 endonuclease which cuts one of the double strands and *E. coli* exonuclease III which digest the nicked strand of DNA. A biotinylated oligonucleotide complementary to a segment of the target cDNA is hybridized with the ssDNA library. Using streptavidin-coupled FMP the specific DNA of interest is captured. After washing twice, the captured ssDNA target is released by elution buffer as is known in the art. The single strand cDNA is converted into dsDNA by DNA-dependent DNA polymerase. The dsDNA is transformed into and amplified in bacteria. The target gene is further identified by other molecular biology techniques, like PCR.

Example VI

This example describes purification of PCR products.

FMP technology can provide a simple and rapid method to purify PCR products. The target gene either in a vector or in a form of cDNA is amplified by PCR using a pair of desired 5' and 3' primers. One of the primers is biotinylated. The PCR product is captured by streptavidin coated FMP. After washing, the captured PCR product is purified from the PCR mixture and ready for further manipulation.

Example VII

This example describes direct cloning and subcloning.

The target DNA is a cloned gene in a vector or transcribed cDNA. The target DNA is amplified by standard PCR but the 5' and 3' primers are biotinylated and contain restriction sites. The PCR products are purified from the PCR mixture by using streptavidin coupled FMP. After washing the particles, the products are released from FMP by restriction enzyme digestion. The products are then directly ligated into a vector and transformed into bacteria.

Example VIII

This example describes RNA/DNA sequencing.

If the starting material is RNA, a cDNA complementary to target RNA is synthesized by a reverse transcriptase. The target DNA is amplified by PCR using desired 5' and 3' primers in which one of them is biotinylated. The biotinylated PCR product is purified by streptavidin coupled FMP. The ssDNA is separated from dsDNA by denaturing whereas the biotinylated ssDNA remain bound to FMP. After washing, the solid-phase linked ssDNA is used as a template to be sequenced by the standard Sanger dideoxy method as is well known from the prior art literature.

Example IX

This example describes single strand oligonucleotide probe labeling.

Oligonucleotide probe labeling is a necessary and essential step in several molecular biology methods, e.g. southern and northern blots, footprint and ribonuclease protection assay. Applying FMP technology to labeling an oligonucleotide probe can simplify the time-consuming labeled probe purification procedure that usually involves multiple steps of phenol extraction, alcohol precipitation and high-speed centrifugation.

The template for the target nucleic acid probe can be bound to FMP either directly by a covalent bond or indirectly via biotin-streptavidin mediated interaction as described in the application of the purification of single stranded DNA. The template could be synthetic oligo nucleic acids (directly), PCR-derived DNA, ssDNA and mRNA. DNA polymerase is used to synthesize the second strand of DNA as a probe in the presence of dNTP mixture as well as radioactive labeled or fluorescent nucleotide bases. The probe associated with FMP is isolated from the reaction mixture by magnetic separation for FMP, or by gravity settling for either FMP or DP, and washed with buffer. The single strand radioactive probe is further separated from FMP by denaturing double strand DNA. The denaturing could be by heating (90° C.) since FMP can be heated to over 250 deg C., alkaline pH or low salt concentration.

Example X

This example describes DNA and RNA binding protein isolation.

FMP can be used to rapidly isolate DNA and RNA binding proteins from lysed cell preparations and lysed nuclear preparations. DNA or RNA probes that contain the binding protein recognizing sequence are directly or indirectly (via biotin/streptavidin and poly(dT)) coupled to FMP as described in the applications of mRNA purification and PCR product purification. The probe-coupled FMP is then added directly to the lysed preparation to capture the nucleic acid binding protein via the mixing and settling procedure disclosed herein. After washing, the highly purified binding protein can be eluted from FMP by high salt, heating or low pH.

Thus, as discussed previously, the invention can involve settling by gravity or being selected magnetically. The particles can be mixed by passing at least once through a sample. Alternatively, the mixing is effected by repeatedly tumbling the particles through the sample, by vortexing end-over-end mixing, nutation, and/or vortexing.

The particles can be formed of ferromagnetic material, optionally nickel. The particles preferably have a diameter of about 0.1 to about 2 microns, and a density of about 9 gm/cm$^3$.

The mixing is carried out for about 15 seconds to about 15 minutes. The magnetic collection is carried out for about 3 seconds to about 4 minutes.

The separation step may include diluting isolated nucleic acids from the particles.

With respect to the biological molecules, they may be, but are not limited to nucleic acids or proteins. More specifically, the biological molecules are a specific DNA sequence or a specific RNA sequence.

The method may be used to purify mRNA, DNA, or DNA or RNA binding proteins, as well as protein/polypeptide fractions.

Detailed Description of the Preferred Embodiments for Large Scale Chromatography Applications According to preferred embodiments the present invention encompasses methods, apparatus, and particle compositions for efficient selection of target biological molecules in a fluid sample.

The invention includes use of both ferromagnetic materials, as opposed to superparamagnetic materials of the art, dense materials and buoyant materials. The particles are used as described herein to capture specific biological molecules, specifically the isolation of specific biological molecules from relatively large volumes. Following capture the separation process is either by gravity, buoyancy or magnetics.

Preferred embodiments are discussed in detail for each type of separation. In general FMP can vary in size from about 100 nanometers to 2 micron for magnetic separation, though particles>10 micron will function for magnetic separation. The upper particle size limit is defined functionally as that size which permits capture of biological molecules as described herein. For gravity separation or buoyancy using DP separation is also defined functionally as above. For gravity separation in particular particles sizes in the range of 0.8 micron to 5 micron are preferred but any size that functions to capture biological molecules prior to gravity settling are anticipated by the invention.

FMP and DP can be made with the appropriate affinity ligand added, and allowed to mix with the target i.e protein containing media, followed by separation of the target protein/particle complex from the media, and subsequent purification. The following describes unique mechanisms for affinity purification of a target recombinant protein, as an example but not limited to, secreted into the media, without the need for media concentration and filtration which represents a significant improvement over the existing art.

Pre-Purification Protocol

The particles are conjugated with an appropriate ligand for affinity chromatography (capture of the target protein). Following the completion of the cell culture phase for production of the recombinant protein, the media is transferred into an appropriately sized vessel for mixing. The mixing vessel can be either a sealed container (e.g. a bottle) or for larger scale cell cultures, the vessel can be open at the top for the insertion of a stirrer.

Example 11

Sealed Container Mixing (Low Volume)—Magnetic Separation

Figures 3A, 3B:
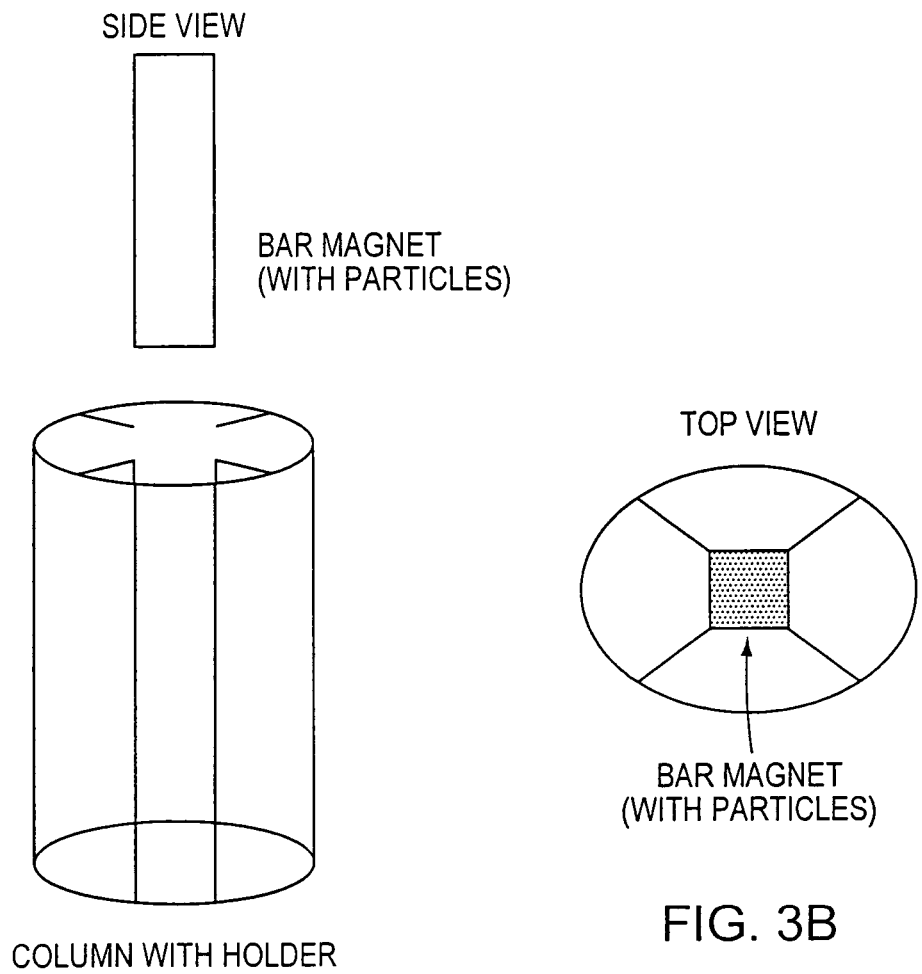
FIGS. 3a and 3b respectively show side and top views of a bar magnet and column with a reaction vessel (mixing capture chamber) to magnetically capture particles.

For cultures of 1 Liter total volume or less, the total reactor content can be removed from the bioreactor and placed in a sealable bottle of appropriate volume. The volume of the container should be such as to allow for mixing of the sample (i.e. be less than the total volume of the container). After the reactor content is placed in the bottle, an appropriate amount of conjugated particles should be placed in the container, and the container is sealed. The container is then mixed by placing it on a mixer (either rotating or end-over-end) for 30 min. to 1 hour. One skilled in the art will appreciate that mixing times will be determined for each application and will be as fast as possible. The mixing speed should be sufficient for vigorous mixing, allowing all of the contents to interact with each other. After mixing, the bottle is immediately placed on a flat surface. The container is opened, and a clean sterilized bar magnet preferably composed of materials described in U.S. Published Application #20040023222 and U.S. Pat. No. 5,186,827 is lowered into the container (FIG. 3a and FIG. 3b) without the magnet touching the bottom. The container is then rotated slowly, for up to 5 min. to ensure that all of the particles in the container come into contact with the magnet. After binding of the particles to the magnet, the unbound material (including cell, debris, media, and unbound proteins) is left in the container and the magnet containing the particles is removed. The magnet with particles bound is then washed three times with buffer, and the magnet is then placed vertically in a column. The column is then loaded with running buffer to remove any unbound proteins, and the bound target protein is then eluted with an appropriate elution buffer common in the art to remove the bound target protein. Thus, the target protein is isolated using FMP that serve both the step of removal of debris and the step of isolation of the desired biological molecule thus alleviating the need for a separate time consuming debris removal step.

For cultures of 1 Liter total volume or less, the total reactor content can be removed from the bioreactor and placed in a sealable bottle of appropriate volume. The volume of the container should be such as to allow for mixing of the sample (i.e. be less than the total volume of the container). After the reactor content is placed in the bottle, an appropriate amount of conjugated particles should be placed in the container, and the container is sealed. The container is then mixed by placing it on a mixer (either rotating or end-over-end) for 30 min. to 1 hour. The mixing speed should be sufficient for vigorous mixing, allowing all of the contents to interact with each other. After mixing, the bottle is immediately placed on a flat surface next to a vertically mounted bar magnet. The bottle is rotated slowly while constantly resting against a magnet for 5 min., which allows for all of the particles to come under the influence of the magnetic field emanating from the magnet. In another configuration the reaction vessel can be placed in a magnetic filed surrounding the vessel and magnetic particles are collected around the vessel surface as described in U.S. Published Application #200400232222 using but not limited to a quadrupole configuration After the particles are localized to the side of the bottle by the magnet, the bottle is opened, and the unbound material (cells, debris, media, unbound proteins) is removed by vacuum aspiration or simply pouring while the bottle is still held against the bar magnet. Isotonic PBS or another appropriate buffer is added to the bottle, and the bottle is sealed and removed from the magnet. The bottle is then mixed end-over-end for 30 sec, and placed back against the bar magnet. The bottle is rotated slowly against the bar magnet as previously described, and the bottle is then opened. The buffer is removed by vacuum aspiration, and the wash process is repeated two additional times. Isotonic PBS is then added to the bottle, and the bottle is removed from the bar magnet. The particles in the bottle are transferred to an appropriately sized column, and additional PBS is added to the bottle to remove all of the particles from the bottle. Once the particles are all in the column, the appropriate running and elution buffers are used to wash any unbound protein, and to elute the target protein from the column.

Example 12

Sealed Container Mixing (Low Volume)—Gravity Settling

The mixing and capture of the desired protein is as in Example 11 but the separation is by gravity settling as defined in the application rather than by magnetics. Following the mixing steps, the vessel is placed upright and particles are allowed to settle to the bottom of the vessel by gravity or by centrifugation. Following the settling step, the solution is removed as discussed in Example 11. If the DP are also magnetic, the particles can be held at the bottom of the tube by a magnet prior to removal of the solution.

Example 13

Open Container Mixing (Large Volume)—Magnetic Separation

For larger volumes, which cannot be conveniently mixed by end-over-end mixing or by rotation, the contents from the bioreactor are placed into an appropriate sized open container. After addition of the appropriate amount of conjugated particles, a non magnetic stirrer is lowered into the container, and the contents are mixed for 10-30 min. at a low speed to ensure proper mixing. Following the mixing step, a vertical bar magnet is placed against the container and moved slowly around the container, while always kept in contact with the side of the container. The non-magnetic stirrer continually mixes the contents slowly while the bar magnet is moved around the container. After the particles are localized to the side of the container by the magnet, the unbound material (cells, debris, media, unbound proteins) is removed by vacuum aspiration while the bar magnet is still held against the outside of the container. Isotonic PBS or another appropriate buffer is added to the container, and the bar magnet is taken away from the container. The non-magnetic stirrer is then used to wash the particles for 5 min. to ensure complete mixing. The bar magnet is then brought against the container and rotated as previously described to ensure localization of the particles to the vicinity of the magnet. The buffer is removed by vacuum aspiration, and the wash process is repeated one to two additional times. Isotonic PBS is then added to the container, and the bar magnet is taken away from the container. The particles in the container are transferred to an appropriately sized column, and additional PBS is added to the container to remove all of the particles from the container. Once the particles are all in the column, the appropriate running and elution buffers are used to wash any unbound protein and to elute the target protein from the column by means known in the art.

Example 14

Placement of Bar Magnet in Vessel

The contents from the bioreactor are placed into an appropriate sized open container. After addition of the appropriate amount of conjugated particles a non magnetic stirrer is lowered into the container, and the contents are mixed for 10-30 min. at a low speed to ensure proper mixing. Following the mixing step, a vertical bar magnet is placed inside the container and held in the container and away from the stirrer. The non-magnetic stirrer continually mixes the contents slowly while the bar magnet is inside the container. After binding of the particles to the magnet, the unbound material (including cell, debris, media, and unbound proteins) is left in the container and the magnet containing the particles is removed. The magnet containing the molecule of interest bound to the ferromagnetic particles is then washed three times with buffer, and the magnet is then placed vertically in a column. The column is then loaded with running buffer to remove any unbound proteins, and the bound target protein is then eluted with an appropriate elution buffer to remove the bound target protein by means known in the art.

Example 15

High Performance Liquid Chromatography (HPLC)

The use of the Nickel metallic particles in the purification of proteins is advantageous in HPLC applications. HPLC is a form of column chromatography used frequently for the isolation of biological molecules. The sample is forced through a column by liquid at high pressure, which decreases the time the separated components remain on the stationary phase and thus the time they have to spread out within the column, leading to broader peaks. Less time on the column then translates to narrower peaks in the resulting chromatogram and thence to better selectivity and sensitivity. These particles are appropriate for use in HPLC as an improvement over the art for the following reasons:

1. Surface area—the particles have a very high surface area (because of their uneven surface as opposed to smooth surfaces seen in particles currently used in HPLC), which allows for the attachment of more affinity binding ligand to the particles, the subsequent binding of more target protein. The additional surface area also makes it easier for protein to make contact with the ligand, and for buffer to make contact with the ligand/protein. The higher surface area also results in greater binding capacity of protein/unit particles, which results in a smaller column needed for a given purification task.

2. Structural Rigidity—the particles are composed of solid nickel with a nickel oxide coating. The particles are very dense and also very hard. This allows for the particles to be used in HPLC which is designed for use under high pressure and high flow rates. The particles should withstand higher pressures than particles currently used in the art for HPLC 3. Particle Size—related to surface area, the particles have a greater surface area that is inversely proportional to total particle volume. Smaller particles have a greater area vs larger particles and are more useful for HPLC due to their greater surface area.

Example 16

Affinity Isolation of Mouse IgG

The method as disclosed herein was used to determine the feasibility, on a small scale, of using ferromagnetic particles for the affinity isolation of proteins. Ferromagnetic nickel particles were labeled as described herein with Goat anti-mouse IgG (GAM-FMP). GAM-FMP was then used to isolate mouse IgG from a buffer solution. 25 ul of GAM FMP were incubated with 1 ug mouse IgG for 30 minutes by mixing end-over-end. The particles were rinsed. Detection of IgG bound to GAM-FMP was measured using Goat anti mouse Horse Radish Peroxidase (HRP) in a standard HRP assay known in the art using optical density of the solution as a measure of binding of IgG to the particles. The background [no IgG present] OD was 0.141 while the OD following binding of IgG (1 ug) was 0.702 indicating that the particles successfully bound the IgG protein confirming the ability of the particles to perform an affinity isolation procedure.

Example 17

Affinity Isolation of a Biological Molecule from Serum

The method as disclosed herein was used to determine the feasibility, on a small scale, of using density particles for the affinity isolation of a protein biomolecule directly from serum. A model system was used. An Avidin-FMP was used to isolate Biotin-labelled Horse Radish Peroxidase (HRP). HRP was assayed as in Example 16. Avidin was directly adsorbed to the particles and the particles were blocked with a blocking agent (bovine serum albumin (BSA)) as described herein to obtain a coated/blocked particle to minimize non-specific binding. Non-specific binding was determined with a BSA blocked FMP without avidin bound. The background signal in the HRP assay was 0.028 indicating very little non-specific binding. 12.5 nanogram biotynylated-HRP was added directly to undiluted serum (200 ul). Avidin-FMP (10 ul) were added to the serum containg the biomolecule of interest (biotynylated-HRP) and mixed end-over-end for 10 minutes. Following mixing the particles were allowed to settle by gravity as defined herein and washed using gravity settling. The particles were then assayed using the HRP assay to measure bound biotynylated-HRP. The signal (Optical density=0.695) was larger than the background signal (0.028) indicating that the Avidin-FMP did successfully bind the desired biomolecule (biotynylated-HRP) by the method disclosed herein.

For additional explanatory information, please refer to the following:

REFERENCES

Website, http://www.proteinchemist.com/tutorial/iec.html
1. Affinity Chromatography Methods and Protocols Bailon, Pascal; Ehrlich, George K; Fung, Wen-Jian; Berthold, Wolfgang Hoffmann-La Roche Inc., Nutley, N.J. 2000
2. Website, http://www.forumsci.co.il/HPLC/topics.html
3. Provisional Application The disclosures of the above references are specifically incorporated by reference herein.

We claim:

1. A plurality of coated particles, said particles comprising:
    ferromagnetic metal particles having a diameter of about 0.1 to about 2 microns and a density of about 9 gm/cm$^3$, having a protective layer to prevent ion leaching wherein said protective layer does not alter the settling and magnetic properties of the particles, and wherein said particles remain magnetic after removal of a magnetic field; and said particles being coated with a blocking agent and at least one binding agent to have predetermined biological molecules bind thereto, said binding agent selected from the group consisting of an antibody, an antigen, a nucleic acid, a complementary nucleic acid, a lectin, a carbohydrate, avidin, biotin, a protein, a glycoprotein, and a lipid.

2. The particles of claim 1, wherein said at least one binding agent specifically binds at least one biological molecule selected from the group consisting of RNA, DNA, protein, glycoprotein, lipid and carbohydrate.

3. The particles of claim 1, wherein said blocking agent coats over sites on the particles that exhibit non-specific binding to biological molecules.

4. The particles of claim 1 wherein said blocking agent is selected from the group consisting of serum albumin, carrageenan, polyglycol and nonionic surfactant.

5. The particles of claim 1, whereas said particles are made of at least one of nickel, cobalt, and iron.

6. The particles of claim 1, wherein said particles are made of at least one of a single metal, an alloy, an organic compound, and a combination of metal and organic compound.

7. The particles of claim 1, for use in a fluid sample comprising at least one of diluted whole blood, undiluted whole blood, diluted serum, undiluted serum, diluted plasma, undiluted plasma, and bone marrow.

8. The particles of claim 1, wherein, said particles comprising:
ferromagnetic metal particles having a diameter of about 0.5 to about 10 microns which settle by gravity in about 5 to about 15 minutes.

9. The particles of claim 8, wherein said at least one binding agent specifically binds at least one biological molecule selected from the group consisting of RNA, DNA, protein, glycoprotein, lipid and carbohydrate.

10. The particles of claim 8, wherein said at least one blocking agent is selected from the group consisting of serum albumin, fractions of carrageenan, polyglycol and nonionic surfactant.

11. The particles of claim 8, whereas said particles are made of at least one of nickel, cobalt, and iron.

12. The particles of claim 8, wherein said particles are made of at least one of a single metal, an alloy, an organic compound, and a combination of metal and organic compound.

13. The particle of claim 8, for use in a fluid sample comprising at least one of diluted whole blood, undiluted whole blood, diluted serum, undiluted serum, diluted plasma, undiluted plasma, and bone marrow.

14. The particles of claim 8, wherein said at least one binding agent is a nucleic acid linked to the coated particles through a polymer linker.

15. The particles of claim 8 wherein said particles comprise nickel.

16. The particles of claim 8 wherein said particles are of a density that said particles will settle out of a fluid sample by the earth's gravitation field, by centrifugation following a mixing step wherein the fluid sample comprises at least one of diluted whole blood, undiluted whole blood, diluted serum, undiluted serum, diluted plasma, undiluted plasma, and bone marrow.

17. The particles of claim 8 wherein said particles are of a density that said particles will be buoyant in a fluid sample wherein the fluid sample comprises at least one of diluted whole blood, undiluted whole blood, diluted serum, undiluted serum, diluted plasma, undiluted plasma, and bone marrow.

18. The particles of claim 1 wherein said particles comprise nickel.

19. The particles of claim 1 wherein said particles are of a density that said particles will settle out of a fluid sample by the earth's gravitation field, by centrifugation following a mixing step wherein the fluid sample comprises at least one of diluted whole blood, undiluted whole blood, diluted serum, undiluted serum, diluted plasma, undiluted plasma, and bone marrow.

20. The particles of claim 1 wherein said particles are of a density that said particles will be buoyant in a fluid sample wherein the fluid sample comprises at least one of diluted whole blood, undiluted whole blood, diluted serum, undiluted serum, diluted plasma, undiluted plasma, and bone marrow.

* * * * *